(12) United States Patent
Schoenfeld

(10) Patent No.: US 7,914,489 B1
(45) Date of Patent: Mar. 29, 2011

(54) SAFETY SYRINGE

(75) Inventor: Joel Schoenfeld, Woodbury, NY (US)

(73) Assignee: Univec International, Inc., Woodbury, NY (US)

( * ) Notice: Subject to any disclaimer, the term of this patent is extended or adjusted under 35 U.S.C. 154(b) by 786 days.

(21) Appl. No.: 11/498,555

(22) Filed: Aug. 3, 2006

(51) Int. Cl.
*A61M 5/50* (2006.01)
(52) U.S. Cl. ........................ 604/110; 604/218
(58) Field of Classification Search ................. 604/192, 604/199, 187, 110, 218, 195, 263
See application file for complete search history.

(56) References Cited

U.S. PATENT DOCUMENTS

| 4,468,223 | A | * | 8/1984 | Minagawa et al. | 604/199 |
| 5,562,623 | A | * | 10/1996 | Shonfeld et al. | 604/110 |
| 6,283,941 | B1 | * | 9/2001 | Schoenfeld et al. | 604/110 |
| 2004/0164570 | A1 | * | 8/2004 | Souza, Jr. | 294/51 |

* cited by examiner

*Primary Examiner* — Nicholas D Lucchesi
*Assistant Examiner* — Laura A Bouchelle
(74) *Attorney, Agent, or Firm* — Levisohn Berger LLP

(57) ABSTRACT

An improved syringe and spring clip therefor used in single use (aspirating and non-aspirating) syringes in which the syringe has an improved, X-shaped nose piece for assisting the attachment of a sheath and an improved spring clip for both ensuring better operation of the single use aspect of the device and for ensuring that only a predetermined amount of medicine is loaded into the syringe when the syringe is loaded with medicine.

4 Claims, 4 Drawing Sheets

SAFETY SYRINGE

BACKGROUND OF THE INVENTION

This invention relates to certain improvements in single use syringes both with and without aspirating mechanisms.

These improvements relate to improvements over certain prior structures which are the subject of prior patents, these being identified as U.S. Pat. No. 5,531,691, entitled Single Use Syringe Assembly, issued Jul. 2, 1996; U.S. Pat. No. 5,562,623, entitled Single Use Syringe Assembly Including Spring Clip Lock and Plunger; and, U.S. Pat. No. 6,283,941, entitled Single Use Syringe With Aspirating Mechanism. The contents of these prior patents are incorporated herein by reference.

These prior patents describe certain improvements relating to the single use syringes both with and without aspirating mechanisms. In the course of working with these syringe structures, certain improvements have been discovered and are the subject of this present application. These are more clearly described in the present specification and associated drawings, and are briefly summarized.

The prior art syringes generally have a front nose piece which is shown and described in the prior art as being cylindrical. It has been discovered that by providing an X-shaped nose piece for the front portion of the syringe, improvements in the operation, manufacturing and functioning of the syringe are achieved. The X-shaped front nose piece permits better centering of the needle on the front of the syringe, easier securement of the cover of the needle after use (to reduce needle "sticks"), and provides easier assembly of the nose piece to the barrel of the syringe because of the use of the arms of the X-shaped nose piece during assembly.

Further, the '941 patent shows and describes a spring locking clip about the plunger, employed as described in that patent. Certain improvements have been made to that spring locking clip making it more effective to manufacture, less expensive and more efficient and secure in its use for the purposes intended in the syringe. These will be described in further detail, but overall there is an improvement in the operation achieved with the changes to the spring lock clip described herein.

Another improvement with respect to the prior art is the ability to ensure that the spring clip is attached at a specific location on the plunger to guarantee that the amount of medicament loading in the barrel of the syringe is always precisely predetermined, i.e., a preset amount, such as 1 cc or 0.5 cc, as appropriate. This is achieved by ensuring that the clip is located at and on a precise and exact ratchet tooth each time the clip is attached to the plunger. As a further aspect of this invention, the clip is provided with a tab which cooperates with a notch in the specific ratchet tooth location so that when the clip is attached to the ratchet, the tab sets in the notch, and if sought to be mechanically attached at any other location, it will not properly set in place because there will be no corresponding notch. This will ensure that the clip is precisely located where desired on the plunger to control the exact amount of dosage loaded into the syringe.

DETAILED DESCRIPTION

Figures 1, 1A:
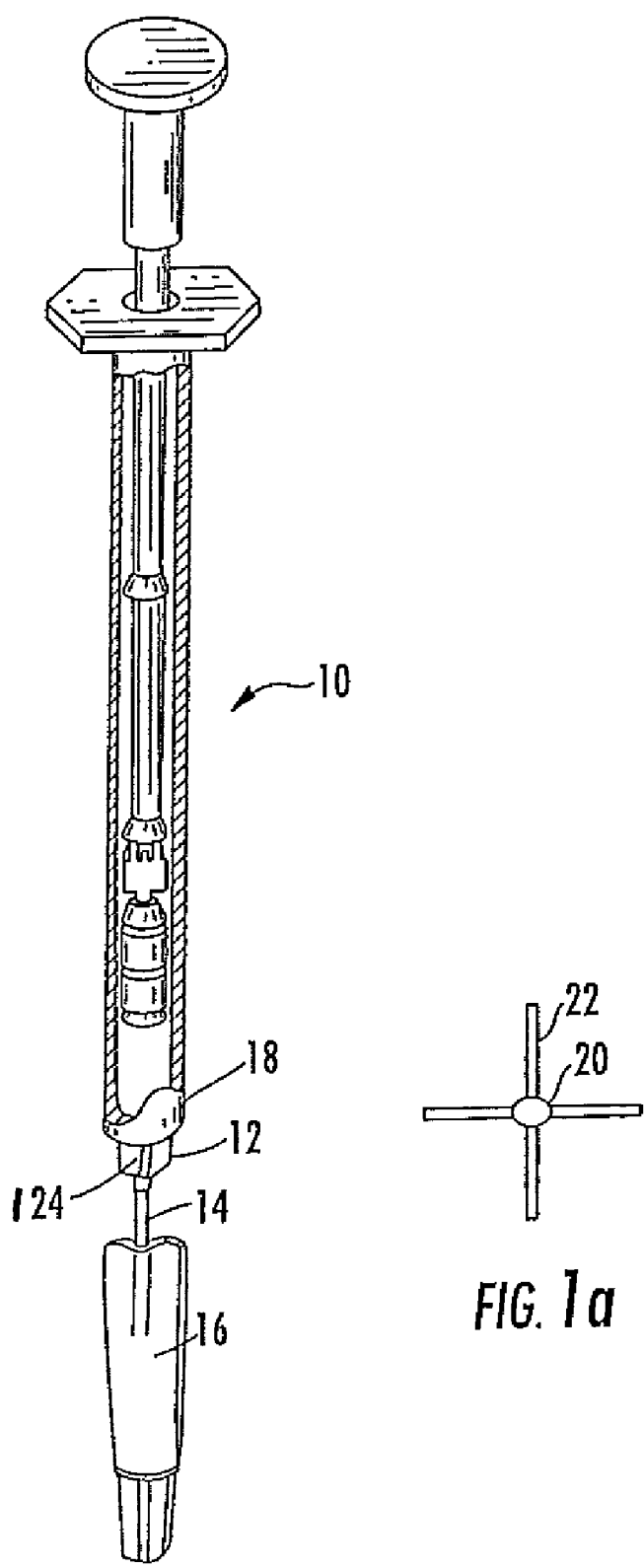
FIG. 1 is a cut away plan view of a syringe with an improved needle front nose piece construction.
FIG. 1a is a front plan view of the improved nose piece section of this invention.

FIG. 1 illustrates a substantially conventional syringe 10 having an improved nose piece 12 with the needle 14 selectively covered by a sheath, cap or cover 16. In the prior art, the nose piece was a cylindrical boss-like structure attached to the bottom of barrel 18. The improvement of the nose piece construction is further illustrated in FIG. 1a which is a front view showing the center 20 of the nose piece 12 with four fins 22 extending 90° with respect to each other. The number of fins could be selected as desired, but each of the fins has slight resilience or flexibility. As shown in FIG. 1, the bottom of each of the fins is slightly mitered or tapered as at 24 so that the sheath 16 may easily be guided up to and slide onto and lock with nose clip 12 by taking advantage of the slight flexibility of fins 22 and the tapered sections 124. Such a nose piece requires less material, assists in the centering of the sheath 16 while being placed and locked on needle 14. The outer dimension of the fins is substantially equal to the inner diameter of the sheath to ensure proper, frictional and secure attachment of the sheath. The modification to nose piece 12 will not involve any new manual manipulation by the user, as it functions, ostensibly, as the prior art nose piece except with the improvements realized and described above. The X-shape of the new nose piece also helps in automatically, i.e., by machine locating the attached needle 14.

Figure 2:
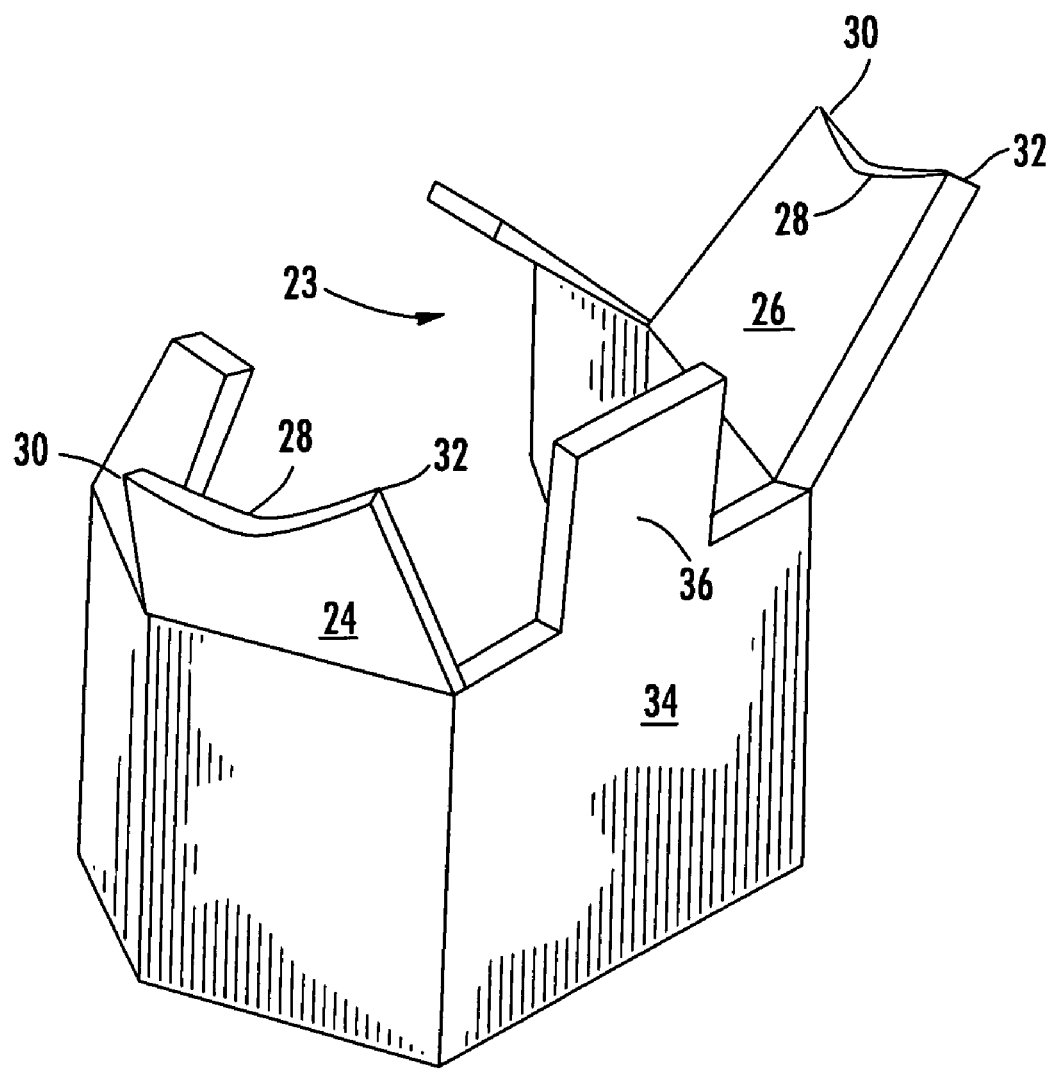
FIG. 2 is a perspective view of the spring clip of this invention.

FIG. 2 is a perspective view of the spring clip which is used in the structure of the prior patents as described therein, attachable to a ratchet tooth of the plunger. The function of the spring clip is to allow for single use only of the syringe whether or not in aspirating form or otherwise. An improvement over the prior art spring clip is realized by changing the outer peripheral structure or profile of locking teeth 24 and 26 by providing a shallow U-shape connection 28 between contact points 30 and 32. This provides improved performance for the spring lock because the prior art sharp triangular or V-shape formed between contact points resulted in a lower stress to be overcome to avoid the single use aspect of the syringe, a result to be avoided. The smoother, rounded connecting arch 28 between sharp contact points 30 and 32 provides for improved performance as the spring lock still is embedded into the side wall of the barrel but its digging-in force is not easily overcome. This prevents against more than a single use of the syringe.

As another feature of this invention, the prior art semicircular tab extended distally and downwardly from back 34 of the clip (which counterbalanced upper tab 36) to prevent jamming of the clip during plunger movement has been eliminated. Because the finishing of the bottom tab was somewhat imperfect, it was found that the plunger would slip, occasionally, and an improvement has resulted by eliminating the bottom tab leaving the bottom wall of the back 34 co-extensive with the entire bottom of the spring clip 23, i.e., co-planar with the other bottom walls of the clip.

Figure 3:
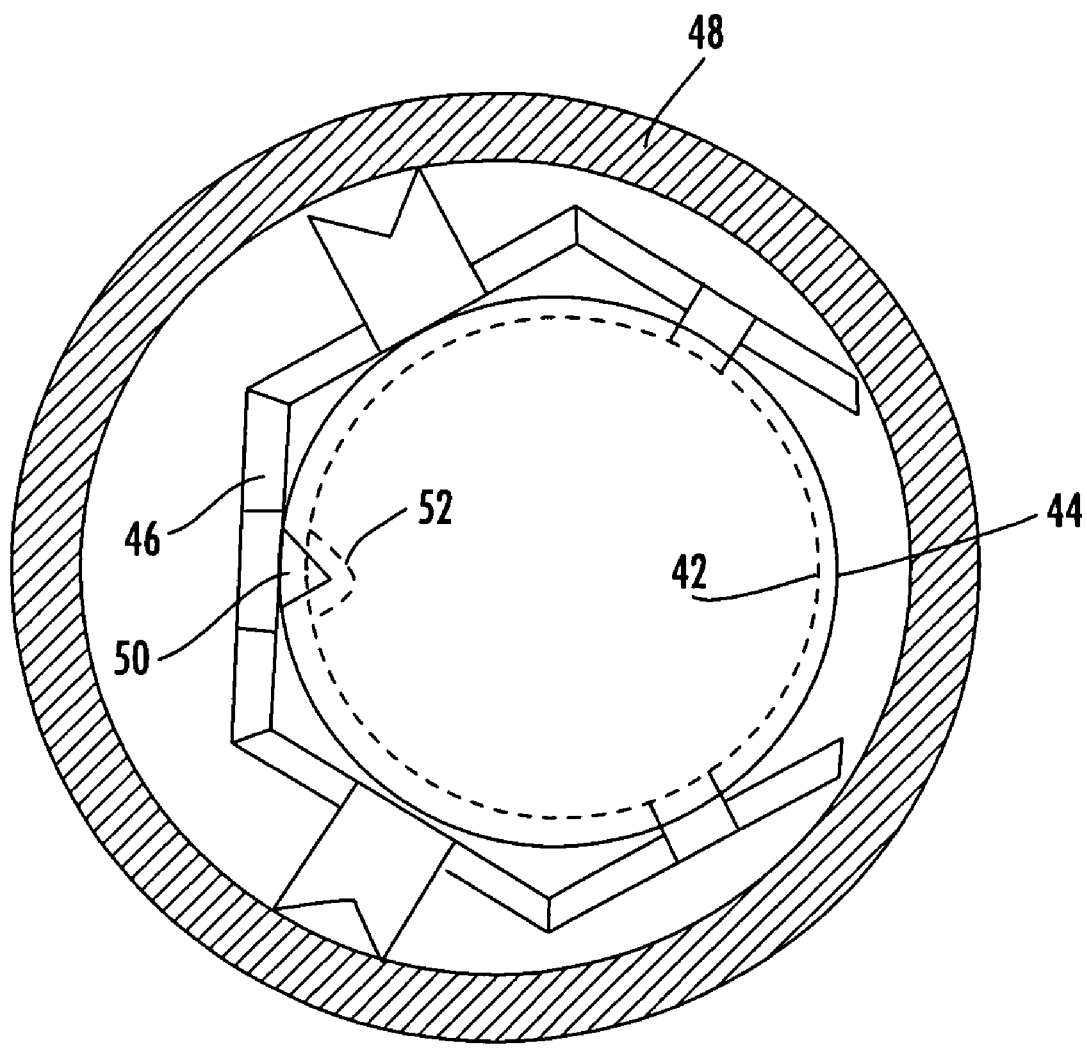
FIG. 3 is a sectional view through the syringe of FIG. 1 showing the spring clip between the barrel and the plunger of the syringe.
Figure 4:
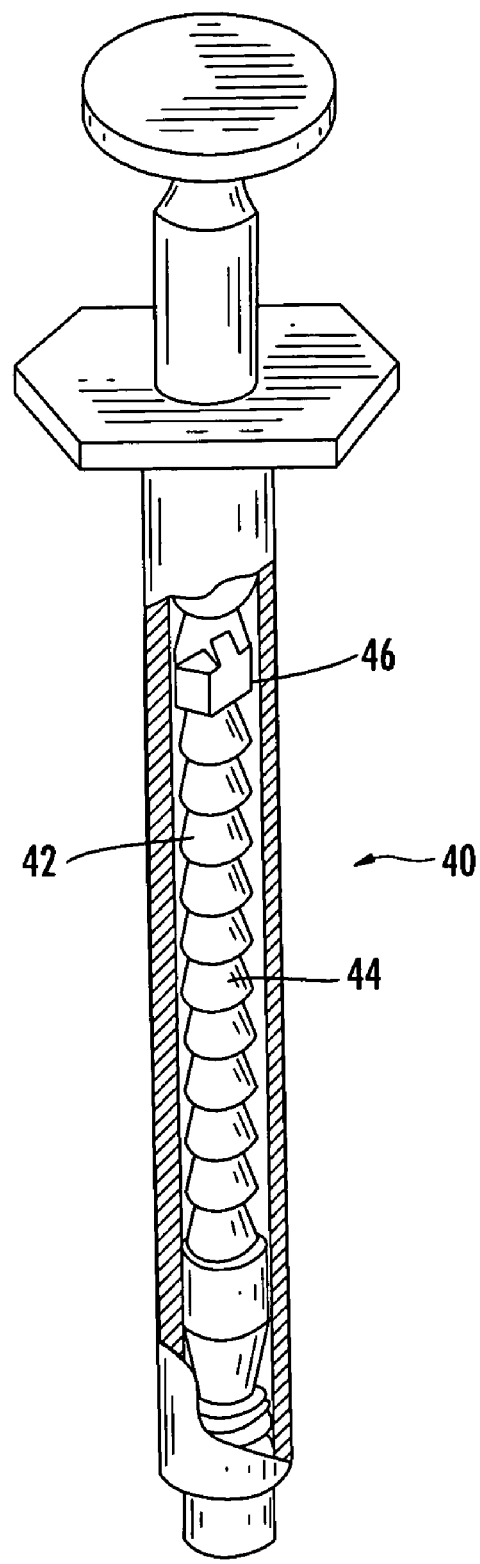
FIG. 4 is a partial cut side plan view showing a specific ratchet tooth to which the spring clip is attached for controlling the amount of medication loading in the syringe.

FIGS. 3 and 4 relate to another aspect of the improvement of this invention. The improvement relates to ensuring that only a precise predetermined amount of medicine is loaded into each syringe. This is made possible by ensuring that the spring lock clip attaches at only one ratchet tooth location along the plunger. Another manner of ensuring such loading is to pre-load a certain predetermined amount of medicine during the manufacturing process relying solely upon such manufacturing controls to pre-load the syringe. Such pre-loaded syringes with preset medicines ensure the reliability of the medical injection by guaranteeing a predetermined amount of medicine is injected each and every time. But more often, syringes are provided empty, for the physician to load and dispense medication. A mechanism is needed to ensure that no more than a precise, predetermined amount of medication can be loaded, at the site of injection, by location of the spring lock clip on the plunger. The prior art did not fix the amount of loaded medicine to be a predetermined amount, and additionally, there was no additional safety to ensure that such predetermined amount was pre-loaded with no more or no less being possible.

FIG. 4 shows a plan elevation view partially cut away showing the plunger with a plurality of ratchet teeth and a clip attached thereto at the predetermined location. In particular, syringe 40 is shown with plunger 42 having a plurality of ratchet teeth 44 one of which is the site for spring clip 46. The spring clip can be attached at only one ratchet because of the structure shown in FIG. 3. In particular, there is shown the barrel 48 of the syringe with the plunger 42 and the ratchet teeth 44 illustrated with the dotted circular lines somewhat inset from the outer edges of plunger teeth 44.

The spring clip 46 is shown attached to the plunger. Further, and in accordance with this invention, an additional tab 50 is formed in the clip, depending inwardly from the inner wall of spring clip 46 to set into a recess or notch 52 formed in the specific or exact ratchet tooth location which will ensure a predetermined amount of medicine can only be loaded into the syringe to be dispensed. Because the tab 50 is integrated to the inner wall of spring clip 46, it will be impossible for the syringe to be properly assembled unless tab 50 fits into the notch 52 of the plunger. Since notch 52 will be at only one location along the barrel (depending on the amount of maximum medication to be loaded), there is only one location for the spring clip to be set on the barrel for proper manufacture and assembly of the syringe of this invention.

It should be understood that the preferred embodiment was described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly legally and equitably entitled.

The invention claimed is:

1. A spring clip for attachment to ratchet teeth of a basically cylindrical plunger of a single-use syringe with said plunger moveable within a barrel of the syringe, the plunger of said syringe moving upwardly and downwardly within the barrel of the syringe, said spring clip locking said plunger so that it is a single use syringe, said spring clip comprising opposed outwardly extending sections having spaced apart contact points to bear into the inner wall of said barrel, and a smooth, rounded arch-like structure connected between said spaced apart contact points, wherein said spring clip comprises a back section and an upwardly extending tab extending therefrom, with the lower clip edge of said spring clip being coplanar around the entire lower periphery of said spring clip, further comprising a tab member extending inwardly from said back section and a complementary notch formed at only one location on said plunger such that said tab of said spring clip connects to said plunger at only said one location along the barrel provided with said notch, said one location comprising a preset location, wherein said preset location along said plunger provides a predetermined volume in said barrel for allowing medicine to be pre-loaded in the syringe be no more than a predetermined amount.

2. The invention of claim 1, wherein said single use syringe comprises a nose piece, said nose piece comprising:

a needle projecting therefrom with a sheath for the needle slid onto the needle and being captured by said nose piece, said nose piece comprising a resilient structure attached at the lower extremity of the barrel, said nose piece comprising:

a plurality of veins extending radially outward from the center thereof, the outward dimension of said veins being substantially equal to the inner diameter of said sheath, such that said sheath slides onto and is held by said veins.

3. The invention as in claim 2, wherein said plurality of veins comprises four veins equally spaced at 90° around said nose piece.

4. The invention as in claim 2, wherein the lower edge of each of said veins is mitered downwardly and inwardly to assist the sheath in sliding onto and being resiliently captured by said nose piece.

* * * * *